US010416047B2

(12) United States Patent
Long et al.

(10) Patent No.: US 10,416,047 B2
(45) Date of Patent: Sep. 17, 2019

(54) ASEPTIC SAMPLING SYSTEM

(71) Applicant: Sentinel Monitoring Systems, Inc., Tucson, AZ (US)

(72) Inventors: Terry D. Long, Tucson, AZ (US); Steven J. Blomquist, Tucson, AZ (US)

(73) Assignee: SENTINEL MONITORING SYSTEMS, INC., Tucson, AZ (US)

(*) Notice: Subject to any disclaimer, the term of this patent is extended or adjusted under 35 U.S.C. 154(b) by 0 days.

(21) Appl. No.: 16/231,118

(22) Filed: Dec. 21, 2018

(65) Prior Publication Data
US 2019/0195750 A1 Jun. 27, 2019

Related U.S. Application Data

(60) Provisional application No. 62/609,200, filed on Dec. 21, 2017.

(51) Int. Cl.
*G01N 1/14* (2006.01)
*A61L 2/10* (2006.01)
*A61L 2/08* (2006.01)
*B01L 3/00* (2006.01)
*G01N 1/18* (2006.01)

(52) U.S. Cl.
CPC ............. *G01N 1/14* (2013.01); *A61L 2/088* (2013.01); *A61L 2/10* (2013.01); *B01L 3/00* (2013.01); *G01N 1/18* (2013.01); *G01N 2001/1427* (2013.01)

(58) Field of Classification Search
CPC .. G01N 1/14; G01N 1/10; G01N 1/18; G01N 2001/1427; B01L 3/00; A61L 2/10; A61L 2/088
See application file for complete search history.

(56) References Cited

U.S. PATENT DOCUMENTS

| 4,785,676 | A  | 11/1988 | DeOca et al. |
| 4,887,472 | A  | 12/1989 | Jansen |
| 5,409,841 | A  | 4/1995  | Chow |
| 6,085,602 | A  | 7/2000  | Schorn et al. |
| 6,423,548 | B1 | 7/2002  | Newberg et al. |
| 6,566,052 | B1 | 5/2003  | Peddada et al. |

(Continued)

OTHER PUBLICATIONS

International Search Report dated Apr. 1, 2019 as received in Application No. PCT/US2018/067384.

(Continued)

*Primary Examiner* — David Z Huang
(74) *Attorney, Agent, or Firm* — Maschoff Brennan

(57) ABSTRACT

A system may include a needle and source providing fluid to the needle. The system may include a sheath defining an opening. The needle may be within the sheath. The needle and sheath may define a cavity. The system may include a gasket movable between open and closed positions. The gasket may fluidly seal an end of the sheath so that the fluid exits the needle into the cavity and exits via the opening. The system may include a bottle including a septum proximate the end of the sheath. The system may include a movement system that may displace the gasket to permit fluid to exit the cavity via the end of the sheath and displace the sheath or needle such that the needle extends beyond the sheath. The movement system may displace the needle or bottle such that the needle penetrates the septum and fluid exits into the bottle.

20 Claims, 9 Drawing Sheets

(56) References Cited

U.S. PATENT DOCUMENTS

| | | |
|---|---|---|
| 6,852,288 B2 | 2/2005 | Newberg |
| 7,241,422 B2 | 7/2007 | Newberg et al. |
| 7,272,980 B2 | 9/2007 | Bigalke |
| 7,437,958 B2 | 10/2008 | Sharma et al. |
| 7,785,304 B2 | 8/2010 | Kashmiran et al. |
| 8,646,342 B2 | 2/2014 | Furey et al. |
| 8,815,179 B2 | 8/2014 | Hofman et al. |
| 2005/0183519 A1* | 8/2005 | Fjerdingstad ............ G01N 1/14 73/864.41 |
| 2007/0056360 A1 | 3/2007 | Grant et al. |
| 2008/0172023 A1 | 7/2008 | Thompson et al. |
| 2010/0288060 A1 | 11/2010 | Ronsick et al. |
| 2014/0170644 A1* | 6/2014 | Hadayer ................. G01N 1/14 435/6.1 |
| 2015/0368606 A1 | 12/2015 | Bishop et al. |
| 2016/0123848 A1 | 5/2016 | Griffin et al. |

OTHER PUBLICATIONS

Written Opinion of the International Searching Authority dated Apr. 1, 2019 as received in Application No. PCT/US2018/067384.

* cited by examiner

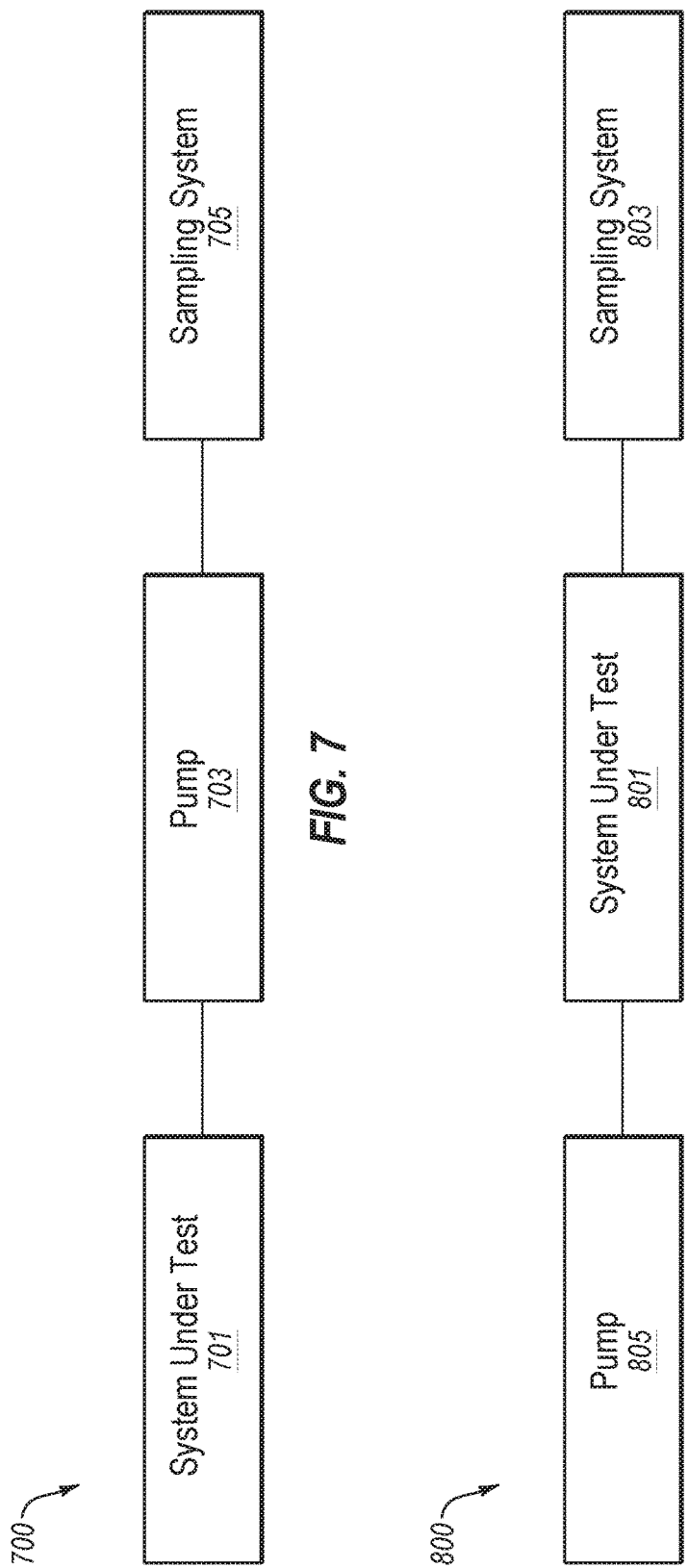

ASEPTIC SAMPLING SYSTEM

CROSS-REFERENCE TO RELATED APPLICATION

This patent application claims the benefit of and priority to U.S. Provisional App. No. 62/609,200 filed Dec. 21, 2017 titled "ASEPTIC SAMPLING SYSTEM," which is incorporated in the present disclosure by reference in its entirety.

FIELD

The embodiments discussed in the present disclosure are related to aseptic sampling systems.

BACKGROUND

Industries that produce fluids to be compliant with health and/or safety standards may monitor the fluid being produced for bacteria and/or other contaminants. If a portion of the fluid appears to be above levels that are compliant with the health and/or safety standards, a sampling system may collect a sample of the fluid for additional testing.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

One or more embodiments of the present disclosure may include a system. The system may include a needle. The system may also include a sample source configured to provide fluid to the needle. In some embodiments, the sample source may be a pressurized fluid system. Additionally, the system may include a sheath assembly that defines an opening. The needle may be disposed within the sheath assembly. The needle and the sheath assembly may define an internal cavity between the needle and the sheath assembly. Furthermore, the system may include a gasket. The gasket may be movable between an open position and a closed position relative to a first end of the sheath assembly. The gasket may be configured to be placed in the closed position to fluidly seal the first end of the sheath assembly to permit the fluid to exit a first end of the needle into the internal cavity and exit the internal cavity via the opening. The system may include a bottle. The bottle may be positioned proximate to the first end of the sheath assembly. The bottle may include a septum configured to fluidly seal an internal cavity of the bottle. The system may also include a movement system. The movement system may be coupled to one or more of the bottle, the sheath assembly, and the gasket. The movement system may be configured to displace the gasket to the open position to permit fluid to exit the internal cavity via the first end of the sheath assembly. The movement system may also be configured to displace the needle relative to the bottle and the sheath assembly to the open position, or displace the bottle and the sheath assembly relative to the needle to the open position such that the first end of the needle extends beyond the first end of the sheath assembly and penetrates the septum and the needle is disposed within the internal cavity of the bottle to permit the fluid to exit the first end of the needle into the internal cavity of the bottle.

The object and advantages of the embodiments will be realized and achieved at least by the elements, features, and combinations particularly pointed out in the claims. Both the foregoing general description and the following detailed description are exemplary and explanatory and are not restrictive.

BRIEF DESCRIPTION OF THE DRAWINGS

Example embodiments will be described and explained with additional specificity and detail through the use of the accompanying drawings in which:

FIG. 7 is a block diagram illustrating an example operating environment of a sampling system; and FIG. 8 is a block diagram of another example operating environment of a sampling system, all according to at least one embodiment described in the present disclosure.

DETAILED DESCRIPTION OF SOME EXAMPLE EMBODIMENTS

Figure 1:
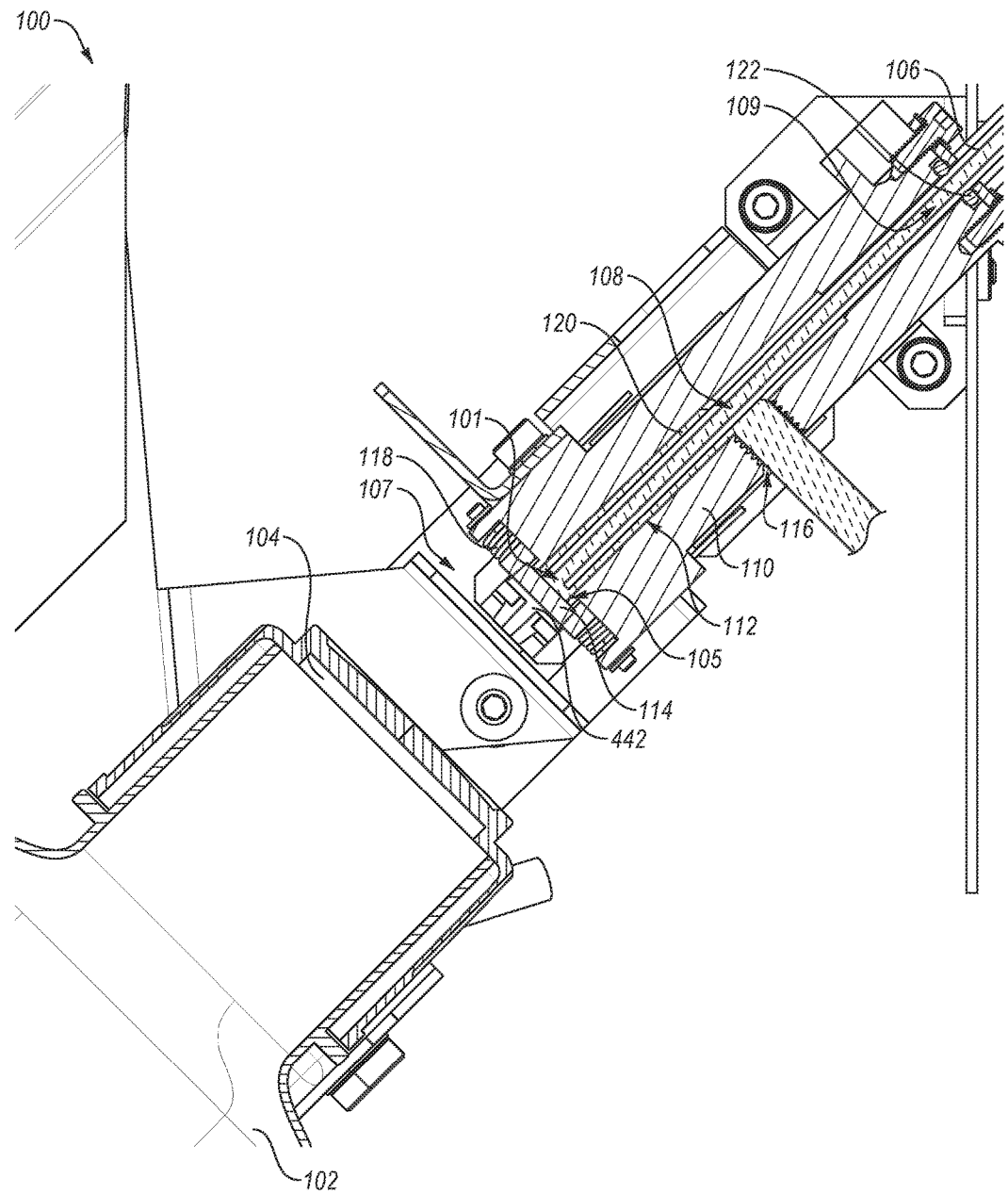
FIG. 1 is a side cross-sectional view of an example sampling system in a closed state.

A sampling system may be configured to facilitate aseptic collection of a sample of a fluid. The sampling system may isolate an internal cavity and/or internal components (e.g., a needle) of the sampling system from an external environment. In some embodiments, the sampling system may be configured to reduce or eliminate bacteria and/or other contaminants that may be present and/or that may develop within the sampling system so as to collect the sample of the fluid without further contaminating the sample of the fluid once it has exited a fluid system.

In some embodiments, the sampling system may be positioned at an angle relative to a direction of gravity so that fluid that contacts one or more external surfaces of the sampling system (e.g., an external surface of a bottle and/or an external surface of a septum) may run off the external surfaces. Additionally or alternatively, positioning the sampling system at the angle relative to the direction of gravity may direct any fluid that escapes the sampling system away from external surfaces of the sampling system (e.g., the external surface of the bottle and/or the external surface of the septum). Furthermore, when a sample of the fluid is to be collected, the external surface of the bottle and/or the external surface of the septum may be rinsed by a portion of the fluid that exits the internal cavity and/or internal components of the sampling system (e.g., a needle) prior to the needle penetrating the septum and the fluid being dispensed in the bottle, which may reduce or eliminate bacteria and/or contaminants from being introduced to the sample of the fluid via the external surface of the bottle.

Alternatively or additionally, the sampling system may be configured to rinse at least a portion of surfaces of the internal cavity including an exterior surface of the needle using the fluid being produced, when the sampling system is in a closed state. For example, when the sampling system is in the closed state, the fluid may enter the internal cavity via the needle and rinse the portion of the surfaces of the internal cavity before exiting the internal cavity via an opening. By rinsing the portion of the surfaces of the internal cavity using the fluid being produced, bacteria and/or other contaminants that may develop on the portion of the surfaces of the internal cavity may be removed from the internal cavity by the fluid. Likewise, rinsing the portion of the surfaces of the internal cavity using the fluid being produced may inhibit the portion of the surfaces of the internal cavity from being exposed to air when the sampling system is in the closed state. Inhibiting the portion of the surfaces of the internal cavity from being exposed to air may inhibit bacteria and/or other contaminants from developing on the portion of the surfaces of the internal cavity. The rinsing may be performed, e.g., continuously, continually, periodically, intermittently, and/or randomly when the sampling system is in the closed state.

Furthermore, the sampling system may be configured to flush the fluid through at least a portion of the internal cavity when the sampling system is in the closed state. For example, when the sampling system is in the closed state, the fluid may continuously enter the internal cavity via the needle and after reaching the opening, the fluid may continuously exit the internal cavity via the opening. By flushing the fluid through the internal cavity, bacteria and/or other contaminants that may be introduced to and/or that may develop within the internal cavity may be removed from the internal cavity. Additionally, continuous movement of the fluid within the internal cavity, when the sampling system is in the closed state, may inhibit bacteria and/or other contaminants from developing within the internal cavity since moving fluid is less likely to develop bacteria and/or contaminants than stagnant fluid.

Alternatively or additionally, the sampling system may include one or more antifouling surfaces and/or light sources to reduce or eliminate bacteria and/or contaminants that may be introduced to and/or that may develop within the internal cavity.

Accordingly, the sampling system may include one or more features or aspects to inhibit and/or reduce bacteria and/or contaminants within the internal cavity. Such features or aspects may include the sampling system being positioned at the angle relative to the direction of gravity such that a surface normal of one or more surfaces of the sampling system is offset from the direction of gravity, one or more components of the sampling system being rinsed, e.g., when the sampling system is in the closed state, antifouling material being included in or on one or more components of the sampling system, and/or one or more light sources that emit UV light into the fluid or onto one or more surfaces of the sampling system. Such features or aspects may be implemented individually in a given sampling system or in any combination.

These and other embodiments of the present disclosure will be explained with reference to the accompanying Figures. In the Figures, features with like numbers indicate like structure and function unless described otherwise. The Figures are diagrammatic and schematic representations of such example embodiments, and are not limiting of the present invention, nor are they necessarily drawn to scale.

FIG. 1 is a side cross-sectional view of an example sampling system 100 (herein system 100) in a closed state in accordance with at least one embodiment disclosed herein. The system 100 may be employed to collect sample fluids to be tested for contaminants. The system 100 may include a needle 106, a sheath assembly 110, and a gasket 114. The system 100 may also include a bottle 102, a spring 118, and an O-ring 122.

The system 100, or at least some components of the system 100, may be positioned at an angle such that a surface normal of one or more surfaces of the sampling system 100 or at least some components of the system 100 may be offset from the direction of gravity. More particularly, the system 100 may be positioned such that a surface normal of the septum 104 may be oriented at an angle substantially not parallel to the direction of gravity (e.g., the surface normal of the septum 104 may be at a non-zero angle relative to the direction of gravity). In some embodiments, the system 100 or one or more components thereof may be positioned such that the surface normal of the septum 104 is oriented at an angle of substantially forty five degrees offset from the direction of gravity or more generally in a range from substantially thirty to substantially sixty degrees offset from the direction of gravity. In other embodiments, the system 100 may be positioned such that the surface normal of the septum 104 is oriented at an angle greater than forty five degrees or less than forty five degrees offset from the direction of gravity. Positioning the system 100 such that the surface normal of the septum 104 is oriented at the angle substantially not parallel to the direction of gravity may inhibit fluid 120 that escapes an internal cavity 112 of the system 100 from reaching the bottle 102 or remaining on the septum 104 or other external surfaces of the bottle 102 if the fluid 120 manages to reach the bottle 102 or the septum 104 (e.g., may prevent the fluid 120 that escapes the internal cavity 112 from pooling on the septum 104 or the external surfaces of the bottle 102).

In other embodiments, the system 100, other systems described herein, and/or one or more components thereof may alternatively or additionally implement one or more of the other features or aspects described herein to inhibit, remove, and/or reduce bacteria and/or contaminants within the internal cavity 112.

The system 100 may be configured to receive the fluid 120 from a sample source (not illustrated). The sample source may be fluidly coupled to the needle 106. The needle 106 may receive the fluid 120 from the sample source and may traverse a needle cavity 108. The fluid 120 may exit the needle cavity 108 via an opening defined by the needle 106 at a first end 101 of the needle 106. In the system 100 illustrated in FIG. 1, the fluid 120 may enter the needle cavity 108 through an opening defined by the needle 106 at a second end (not illustrated) of the needle 106 and the fluid 120 may exit the needle cavity 108 through the opening defined by the needle at the first end 101 of the needle 106. In some embodiments, the needle 106 may include a cannula.

In the closed state of the system 100, the needle 106 may be disposed at least partially within the sheath assembly 110. An external surface of the needle 106 and an internal surface of the sheath assembly 110 may define the internal cavity 112. Additionally, the sheath assembly 110 may define an opening 116 or outlet port. The opening 116 may be fluidly coupled to the internal cavity 112. In the closed state of the system 100, the gasket 114 may be positioned proximate a first end 105 of the sheath assembly 110. The gasket 114 may be movable between an open position (e.g., an open state or a collecting state of the system 100) and a closed position (e.g., the closed state of the system 100 as illustrated in FIG.

1) relative to the first end 105 of the sheath assembly 110. In some embodiments, the gasket 114 may include a polymer gasket.

In the closed state of the system 100, the gasket 114 may fluidly seal the first end 105 of the sheath assembly 110 so as to inhibit the fluid 120 from exiting the internal cavity 112 via the first end 105 of the sheath assembly 110. Additionally, in the closed state of the system 100, the fluid 120 may collect within the internal cavity 112 and may exit the internal cavity 112 via the opening 116. For example, the fluid 120 may exit the first end 101 of the needle 106 and collect in/fill the internal cavity 112 until the fluid 120 reaches the opening 116 and exits the internal cavity 112 via the opening 116. The opening 116 may be located above the first end 101 of the needle 106 relative to the direction of gravity.

The spring 118 may be configured to urge the gasket 114 via a control arm 442 (discussed in more detail below) towards the closed position. In some embodiments, the spring 118 may be part of a movement system 107 including multiple components coupled to one or more of the bottle 102, the sheath assembly 110, and the gasket 114. The movement system 107 may be configured to position and/or move various components of the system 100 in and/or between the closed position and the open position. The movement system 107 is discussed in more detail below.

The O-ring 122 may fluidly seal a second end 109 of the sheath assembly 110 permitting the sheath assembly 110 to move relative to the needle 106 without fluid inadvertently escaping the internal cavity 112 via the second end 109 of the sheath assembly 110.

In the closed state of the system 100, the bottle 102 may be positioned proximate the first end 105 of the sheath assembly 110. The septum 104 of the bottle 102 may fluidly seal an internal cavity of the bottle 102. In some embodiments, the bottle 102 and/or the septum 104 may be configured for one time use to collect the sample of the fluid 120. In some embodiments, the bottle 102 and/or the septum 104 may be configured for multiple uses to collect the sample of the fluid 120.

In the closed state of the system 100, the first end 101 of the needle 106 may be positioned proximate the gasket 114. For example, the first end 101 of the needle 106 may be positioned between fifteen and twenty five millimeters (mm) away from the gasket 114. In the closed state of the system 100, the fluid 120 may enter the internal cavity 112 via the first end 101 of the needle 106 and may collect in/fill the internal cavity 112. The fluid 120 may collect in/fill in the internal cavity 112 and rise towards the opening 116. When the fluid 120 reaches the opening 116, the fluid 120 may exit the internal cavity 112 via the opening 116. In some embodiments, the fluid 120 after exiting the internal cavity 112 via the opening 116 may be directed back into the sample source. In other embodiments, the fluid 120 after exiting the internal cavity 112 via the opening 116 may be discarded.

FIG. 1 and other Figures herein depict the bottle 102 for collecting sample fluids. Other embodiments may implement other fluid collection means instead of or in addition to the bottle 102. For instance, one or more embodiments may implement an intravenous (IV) bag, a tube, or some other container with a septa closure in place of the bottle 102.

Figure 2:
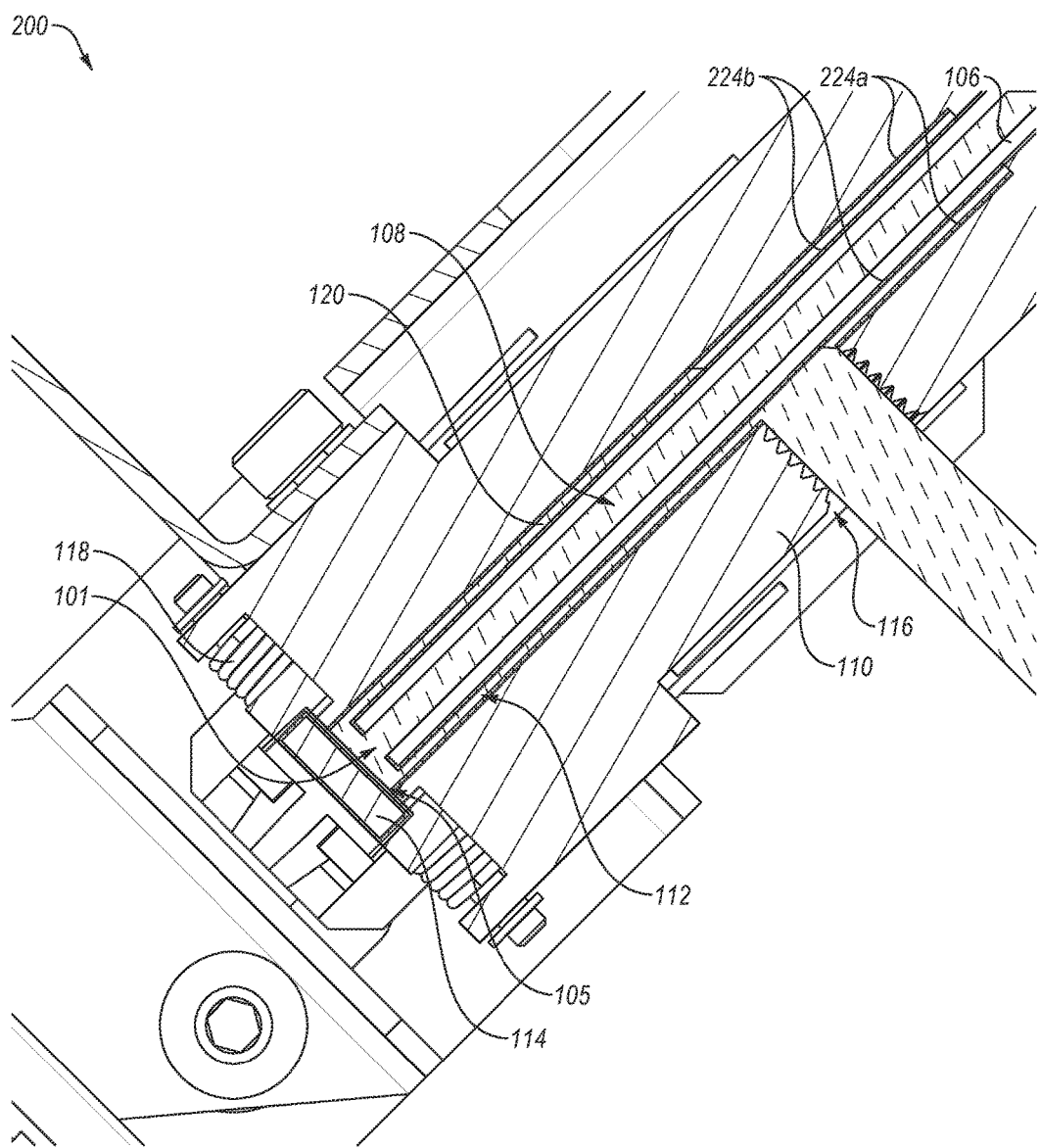
FIG. 2 is a side cross-sectional view of another example sampling system in the closed state.

FIG. 2 is a side cross-sectional view of another example sampling system 200 (herein system 200) in the closed state in accordance with at least one embodiment disclosed herein. The system 200 may be employed in collecting sample fluids to be tested for contaminants. The system 200 may be the same as or similar to the system 100 discussed above in relation to FIG. 1 and may include some or all of the same components and/or features, such as the needle 106, the sheath assembly 110, the gasket 114, the spring 118, the internal cavity 112, and the opening 116. The system 200 may have an open state (not shown in FIG. 2) that is the same as or similar to the open state of one or more other systems described herein. Thus, the system 200 may have one or more components, such as the gasket 114, that are movable between the closed position and the open position.

In some embodiments, the system 200 may also include at least one of a first antifouling coating 224a and a second antifouling coating 224b (collectively 'antifouling coatings 224').

As described above, the fluid 120 may be received by the needle 106. Additionally, the fluid 120 may traverse the needle cavity 108 and exit the needle 106 into the internal cavity 112. Furthermore, the fluid 120 may collect within the internal cavity 112 until the fluid 120 reaches the opening 116. The fluid 120 may exit the internal cavity 112 via the opening 116.

Additionally, one or more surfaces of the system 200 may include and/or have formed thereon the antifouling coatings 224. In some embodiments, the internal surface of the sheath assembly 110 may include the second antifouling coating 224b. Additionally or alternatively, the external surface of the needle 106 may include the first antifouling coating 224a. The antifouling coatings 224 may include any antifouling material or material treatment configured to inhibit bacteria and/or other contaminants from developing. For example, the antifouling material may include one or more of silver, copper, gold, zinc, titanium, alloys of any of the foregoing: organosilanes; quaternary ammonium compounds; fluorocarbons; parylene and photocatalytic materials, or other suitable antifouling material(s). In some embodiments, the antifouling coatings 224 may be positioned downstream of the needle cavity 108 (e.g., the antifouling coatings 224 may come in contact with the fluid 120 after the fluid 120 has exited the needle 106 either into the internal cavity 112 or into the bottle 102). Additionally or alternatively, the gasket 114 may be infused with antifouling material. For example, the gasket 114 may be implemented as a polymer gasket and may be infused with one or more of silver, copper, gold, zinc, titanium, alloys of any of the foregoing: organosilanes; quaternary ammonium compounds; fluorocarbons; parylene and photocatalytic materials, or other suitable antifouling material(s).

In some embodiments, the needle 106 and/or the sheath assembly 110 may be coupled to one or more heat sources (not illustrated). The heat sources may be configured to directly heat the needle 106 and/or the sheath assembly 110. Heating the needle 106 and/or the sheath assembly 110 may inhibit bacteria and/or other contaminants from developing in the fluid 120 or on the surfaces of the internal cavity 112. Additionally, heating the needle 106 and/or the sheath assembly 110 may sanitize the surfaces of the needle 106 and/or the sheath assembly 110. The heating of the needles 106 and/or the sheath assembly 110 may be performed, e.g., continuously, continually, periodically, intermittently, and/or randomly when the sampling system 200 is in the closed state or in the open state.

Figure 3:
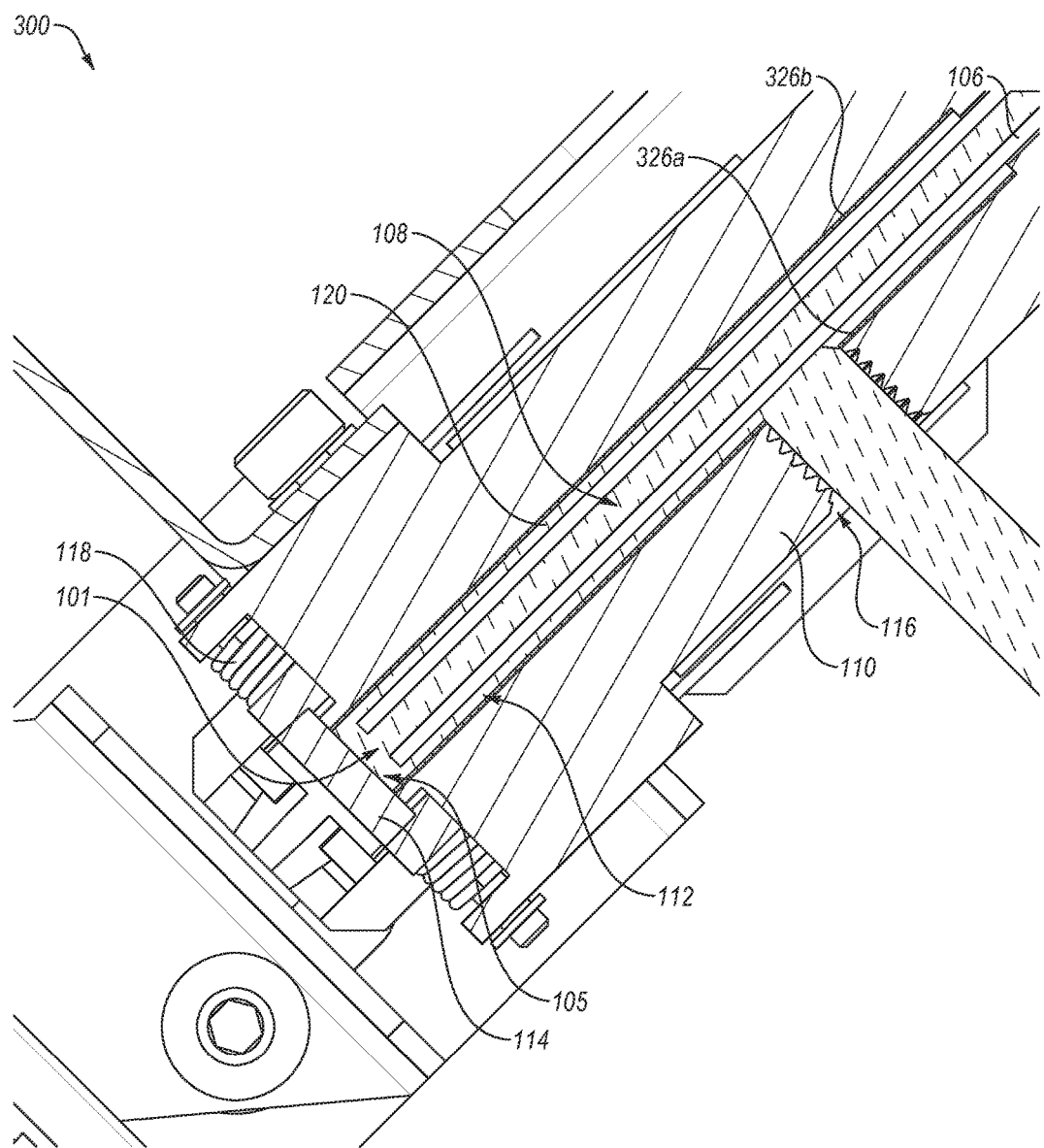
FIG. 3 is a side cross-sectional view of yet another example sampling system in the closed state.

FIG. 3 is a side cross-sectional view of yet another example sampling system 300 (herein system 300) in the closed state in accordance with at least one embodiment disclosed herein. The system 300 may be employed in collecting sample fluids to be tested for contaminants. The system 300 may be the same as or similar to the systems 100 and 200 discussed above in relation to FIGS. 1 and 2 and may include some or all of the same components and/or features, such as the needle 106, the sheath assembly 110, the gasket 114, the spring 118, the internal cavity 112, and the opening 116. The system 300 may have an open state (not shown in FIG. 3) that is the same as or similar to the open state of one or more other systems described herein. Thus, the system 300 may have one or more components, such as the gasket 114, that are movable between the closed position and the open position.

In some embodiments, the system 300 may additionally include at least one of a first light source 326a and a second light source 326b (collectively 'light sources 326').

The fluid 120 may be received by the needle 106. Additionally, the fluid 120 may traverse the needle cavity 108 and exit the needle 106 into the internal cavity 112. Furthermore, the fluid 120 may collect within the internal cavity 112 until the fluid 120 reaches the opening 116. The fluid 120 may exit the internal cavity 112 via the opening 116.

The light sources 326 may be positioned in such a manner as to emit light into at least a portion of the fluid 120 within the internal cavity 112. Additionally or alternatively, the light sources 326 may be positioned in such a manner as to emit light onto at least a portion of the external surface of the needle 106 or onto the internal surface of the sheath assembly 110 (e.g., surfaces of the internal cavity 112). The light may be emitted into the fluid 120 and/or onto the surfaces of the internal cavity 112 to inhibit bacteria and/or other contaminants from developing in the fluid 120 or on the surfaces of the internal cavity 112.

The light emitted by the light sources 326 may include UV light in the range of two hundred sixty to two hundred ninety nanometers (nm). In some embodiments, the first light source 326a and the second light source 326b may include different light pipes positioned at different locations along the internal surface of the sheath assembly 110. In some embodiments, the light pipes may include polymeric material or any other acceptable material for emitting UV light. Additionally or alternatively, the light sources 326 may include a single light source that directs light onto a portion of or onto the entire interior surface of the sheath assembly 110. The light sources 326 may work in combination with the surface coatings 224 as would be the case for photocatalytic surface treatment. For example, the system 300 of FIG. 3 may be modified to include the antifouling coatings 224 and/or the heat sources configured to heat the needle 106 and/or the sheath assembly 110 of FIG. 2, and/or the system 200 of FIG. 2 may be modified to include the light sources 326 of FIG. 3.

Figure 4A:
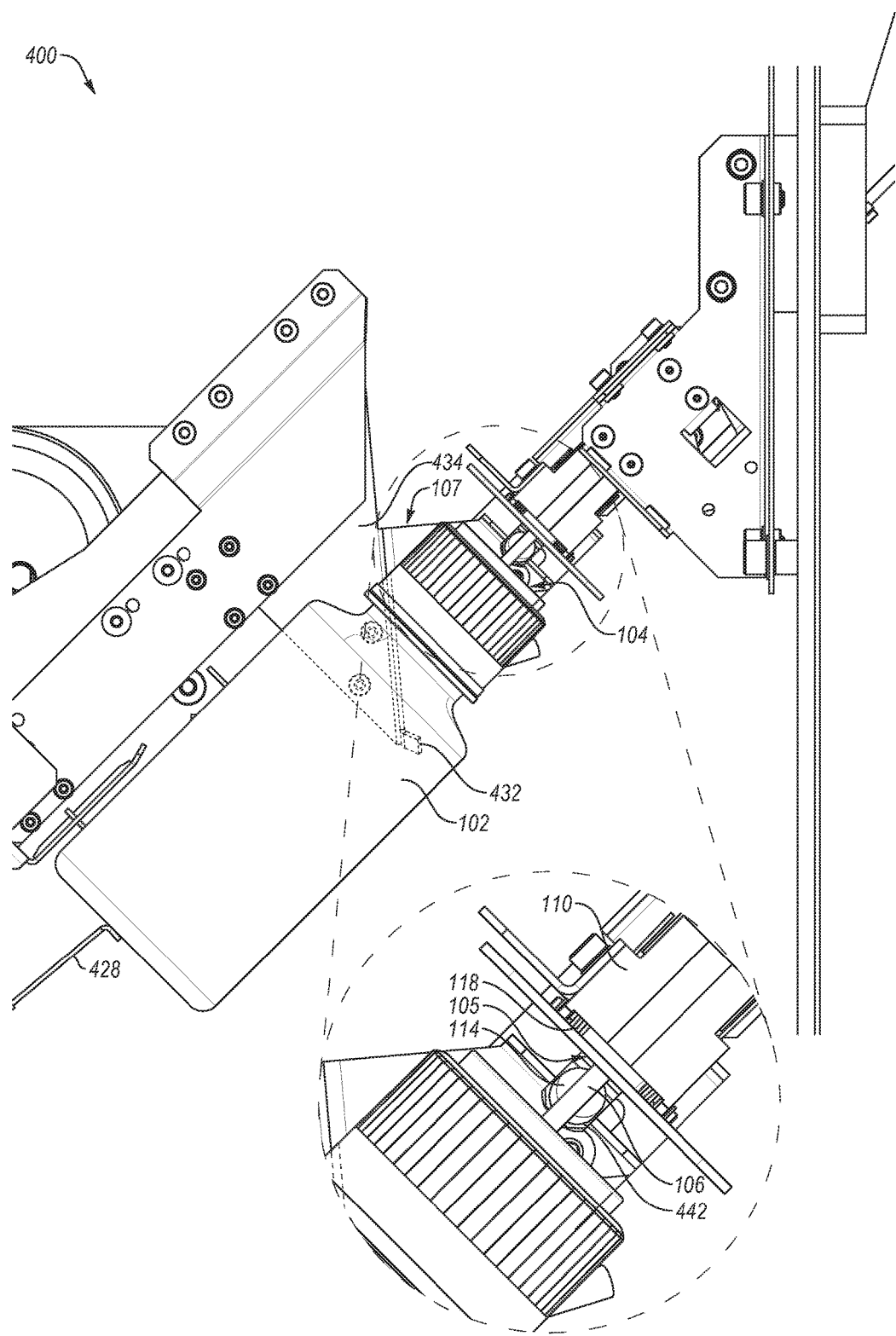
FIGS. 4A, 4B, and 4C are, respectively, perspective side, detailed perspective side, and detailed top perspective views of an example sampling system in an open state.
Figure 4B:
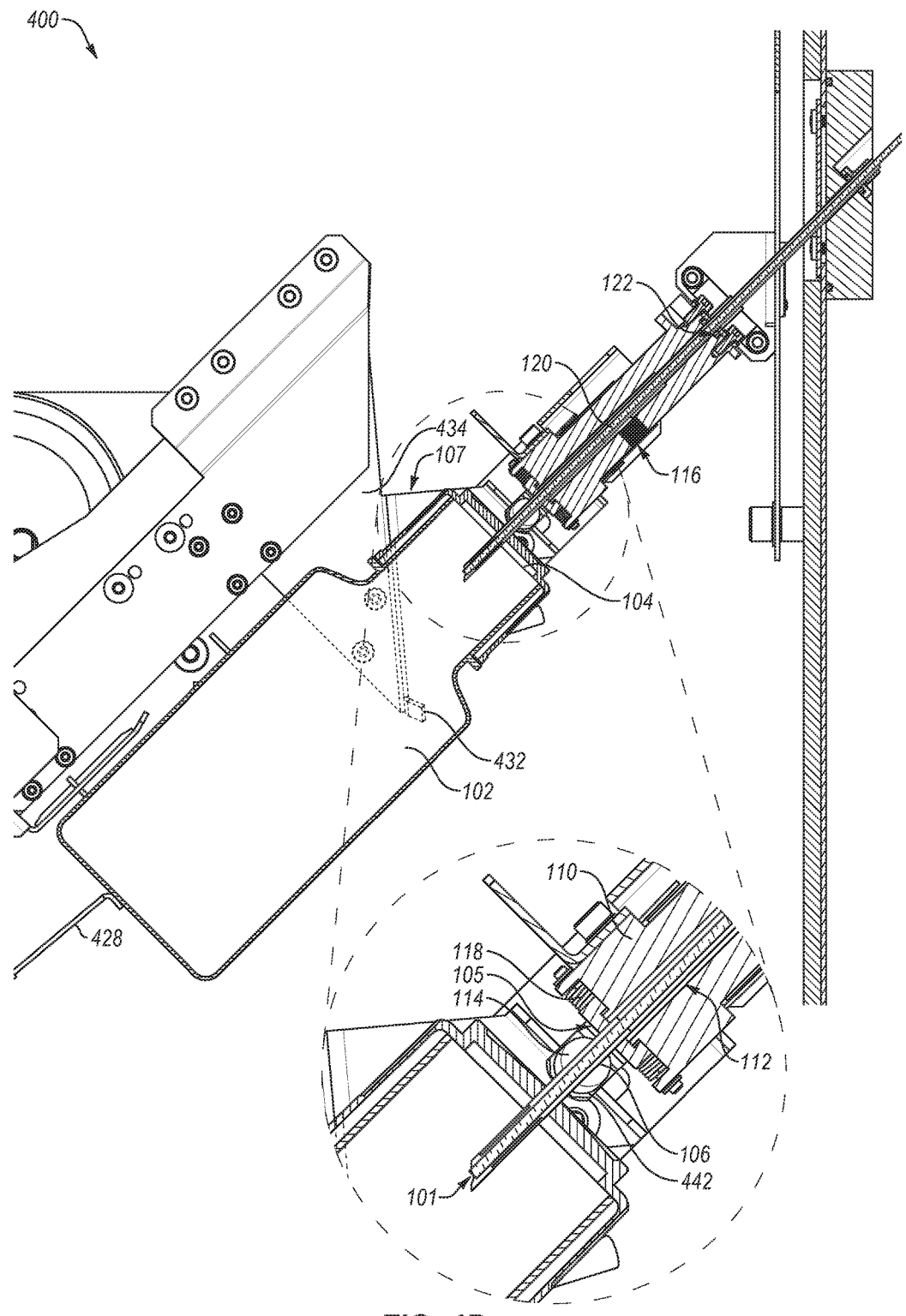
Figure 4C:
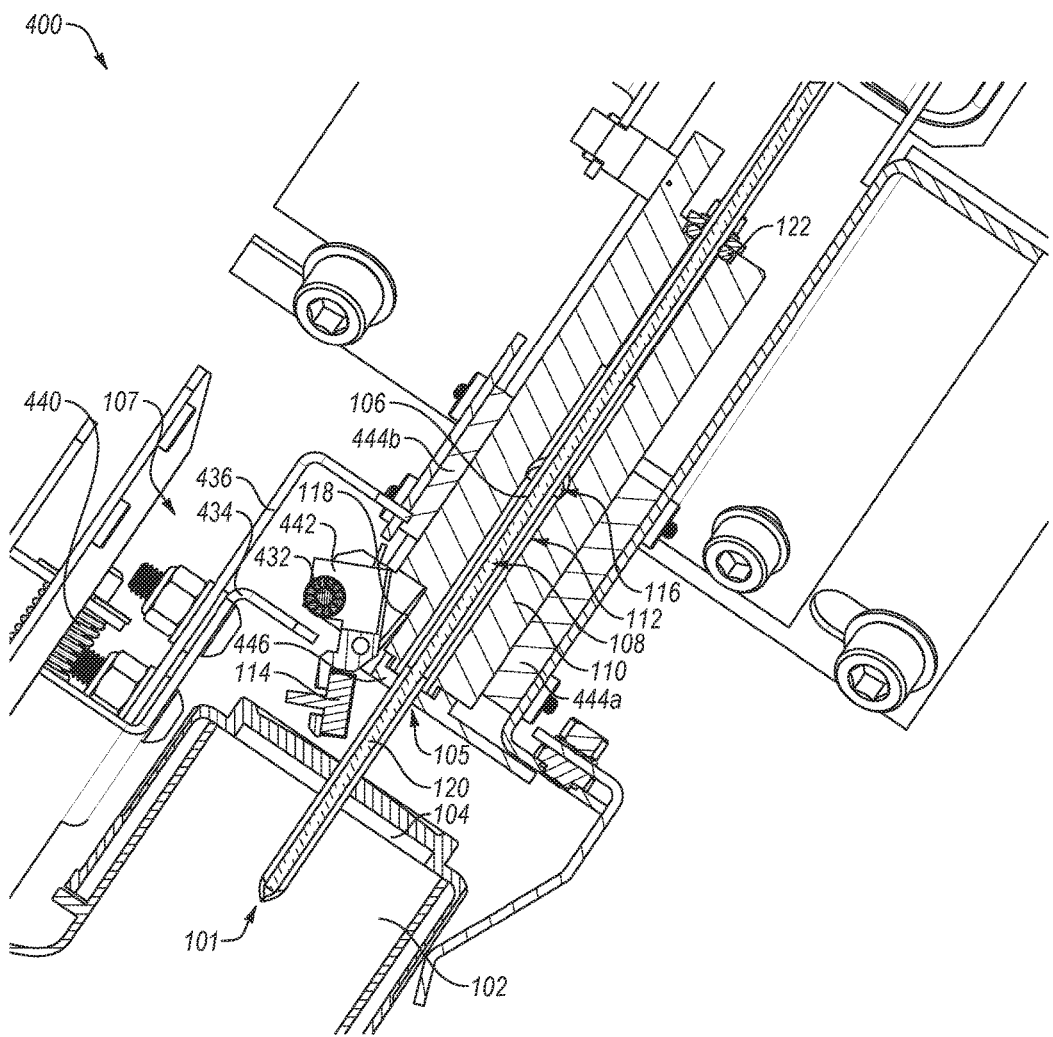

FIGS. 4A, 4B, and 4C are, respectively, perspective side, detailed perspective side, and detailed top perspective views of an example sampling system 400 (herein system 400) in an open state (e.g. a collecting state) in accordance with at least one embodiment disclosed herein. The system 400 may be the same as or similar to the systems 100, 200, and 300 discussed above in relation to FIGS. 1-3, and is illustrated in the open state (e.g., one or more components in the open position) rather than in the closed state as illustrated in FIGS. 1-3. The system 400 may also have a closed state that is the same as or similar to the closed state of the systems 100, 200, and 300 illustrated in FIGS. 1-3. One or more components of the system 400 may be movable between the closed position and the open position. With combined reference to FIGS. 4A-4C, the system 400 may be employed in collecting sample fluids to be tested for contaminants.

The system 400 may include some or all of the same components and/or features as the systems 100; 200; and 300, such as the bottle 102, the septum 104, the needle 106, the sheath assembly 110, the spring 118, the gasket 114, and the O-ring 122. The system 400 may also include a bottle retention device 428, a contactor plate 434, a return plate 436, a wheel 438, a return spring 440, the control arm 442, and at least one of a first guide rail 444a and a second guide rail 444b (collectively 'guide rails 444'). Additionally, the system 400 may be arranged at the angle relative to the direction of gravity, the same as or similar to the systems 100, 200, and 300.

The system 400 may include the movement system 107 configured to position various components of the system 400 in the open position and/or configured to move one or more components of the system 400 between closed and open positions. The movement system 107 may include the spring 118, the bottle retention device 428, the contactor plate 434, the return plate 436, the wheel 438, the return spring 440, and/or the control arm 442.

The bottle retention device 428 may be configured to retain the bottle 102 at an orientation and/or position appropriate for collecting the sample fluid. The bottle retention device 428 may be in contact with the bottle 102 such that when the bottle retention device 428 is being displaced, the bottle 102 is also being displaced. The contactor plate 434 may include a contactor portion 432 (shown, e.g., in FIGS. 4A and 4B), which may be in contact with an external surface of the bottle 102. The bottle 102 may contact the contactor portion 432 such that when the bottle 102 is being displaced the contactor plate 434 is also being displaced. Displacement of the contactor plate 434 may load the return spring 440.

The wheel 438 (shown, e.g., in FIG. 4C) may be in contact with a surface of the contactor plate 434. The wheel 438 may be positioned on the control arm 442 (shown, e.g., in FIGS. 4A, 4B, and 4C). The wheel 438 may permit the control arm 442 to rotate (e.g., transition from the closed position (shown, e.g., in FIGS. 1-3) to the open position (shown, e.g., in FIGS. 4A, 4B, and 4C)) by rolling along the surface of the contactor plate 434. The control arm 442 may rotate relative to a center axis of the spring 118. For example, the contactor plate 434 may contact the wheel 438 when being displaced to the open position, which may cause the wheel 438 to roll along the surface of the contactor plate 434 and cause the control arm 442 to rotate relative to the spring 118.

The gasket 114 may be mechanically coupled to the control arm 442 in such a way that the rotation of the control arm 442 may position the gasket 114 in the open position. The internal cavity 112 may be exposed to an external environment when the gasket 114 is in the open position.

The rotation of the control arm 442 may load the spring 118 which may urge the control arm 442 towards the closed position. The contactor plate 434, while in the open position, may prevent the control arm 442 from transitioning to the closed position.

In the open position, the first end 105 of the sheath assembly 110 may not be fluidly sealed by the gasket 114, which may permit at least a portion of the fluid 120 within the internal cavity 112 to exit the internal cavity 112 via the first end 105 of the sheath assembly 110. The fluid 120 that exits the internal cavity 112 via the first end 105 of the sheath assembly 110 may rinse the septum 104 of the bottle 102. The fluid 120 that exits the internal cavity 112 via the first end 105 of the sheath assembly 110 may not pool on the septum 104 due to the bottle 102 and/or the septum 104 being positioned at the angle relative to the direction of gravity. Additionally or alternatively, a portion of the fluid 120 within the internal cavity 112 may exit the internal cavity 112 via the opening 116 defined by the sheath assembly 110 when the gasket 114 is in the open position (e.g., is no longer fluidly sealing the internal cavity 112).

When the control arm 442 is in the open position, the contactor plate 434 may contact a movement portion 446 (shown, e.g., in FIG. 4C) of the sheath assembly 110 such that positioning of the contactor plate 434 may position the sheath assembly 110 in the open position. For example, as the contactor plate 434 is moved and in contact with the movement portion 446 of the sheath assembly 110, it may cause the sheath assembly 110 to move with the contactor plate 434. The guide rails 444 may be configured to control positioning of the sheath assembly 110. For example, the guide rails 444 may permit the sheath assembly 110 to move in one dimension, e.g., in a direction parallel to the length of the needle 106, in response to movement of the contactor plate 434 while in contact with the movement portion 446.

In the open position, the needle 106 may extend beyond the first end 105 of the sheath assembly 110. Additionally, the bottle 102 may be displaced at least until the needle 106 penetrates the septum 104 of the bottle 102. Penetration of the septum 104 by the needle 106 may remove bacteria and/or contaminants on the needle 106. For example, the septum 104 may scrape the external surface of the needle 106 so as to clean the needle 106 during penetration and prevent bacteria and/or contaminants from being introduced to the fluid 120 within the bottle 102. In the open position, the first end 101 of the needle 106 may be disposed within the bottle 102, as illustrated in FIG. 4C.

In the open position, the fluid 120 may be received by the needle 106 from the sample source. The fluid 120 may traverse the needle cavity 108 and may exit the first end of the needle 106. The fluid 120 may enter the bottle 102 and may be collected up to a desired volume.

After collecting the sample portion, the movement system 107 may displace the various components of the system 400 to the closed position, which may cause the system 400 to transition to the closed state (as illustrated in FIGS. 1-3). For example, the return spring 440 may be loaded when the system 400 is in the open state and may urge the return plate 436 towards the closed position. Displacement of the return plate 436 to the closed position may displace the sheath assembly 110 to the closed position by applying force on the movement portion 446. Additionally, displacement of the return plate 436 to the closed position may displace the contactor plate 434 and the contactor portion 432 to the closed position. Displacement of the contactor portion 432 to the closed position may displace the bottle 102 to the closed position by applying a force on the external surface of the bottle 102. Furthermore, displacement of the return plate 436 to the closed position may displace the bottle retention device 428 to the closed position via the contactor plate 434.

The bottle 102, in the closed position, may be positioned such that the first end 101 of the needle 106 may be positioned external to the bottle 102 and may no longer be disposed in the bottle 102, e.g., as illustrated in FIGS. 1-3. Additionally, the sheath assembly 110, in the closed position, may be positioned such that the needle 106 may be disposed within the sheath assembly 110.

Additionally, displacement of the return plate 436 to the closed position may displace the contactor plate 434 such that the spring 118 may release and displace the control arm 442 and the gasket 114 to the closed position, which may fluidly seal the first end 105 of the sheath assembly 110.

In some embodiments, the bottle 102 and the sheath assembly 110 are displaced relative to the needle 106 between the open position and the closed position, e.g., as described. In some embodiments, the needle 106 may be displaced relative to the bottle 102 and/or the sheath assembly 110 between the open position and the closed position. In these and other embodiments, the gasket 114 may be positioned to the open position prior to the needle 106 being displaced.

Figure 5:
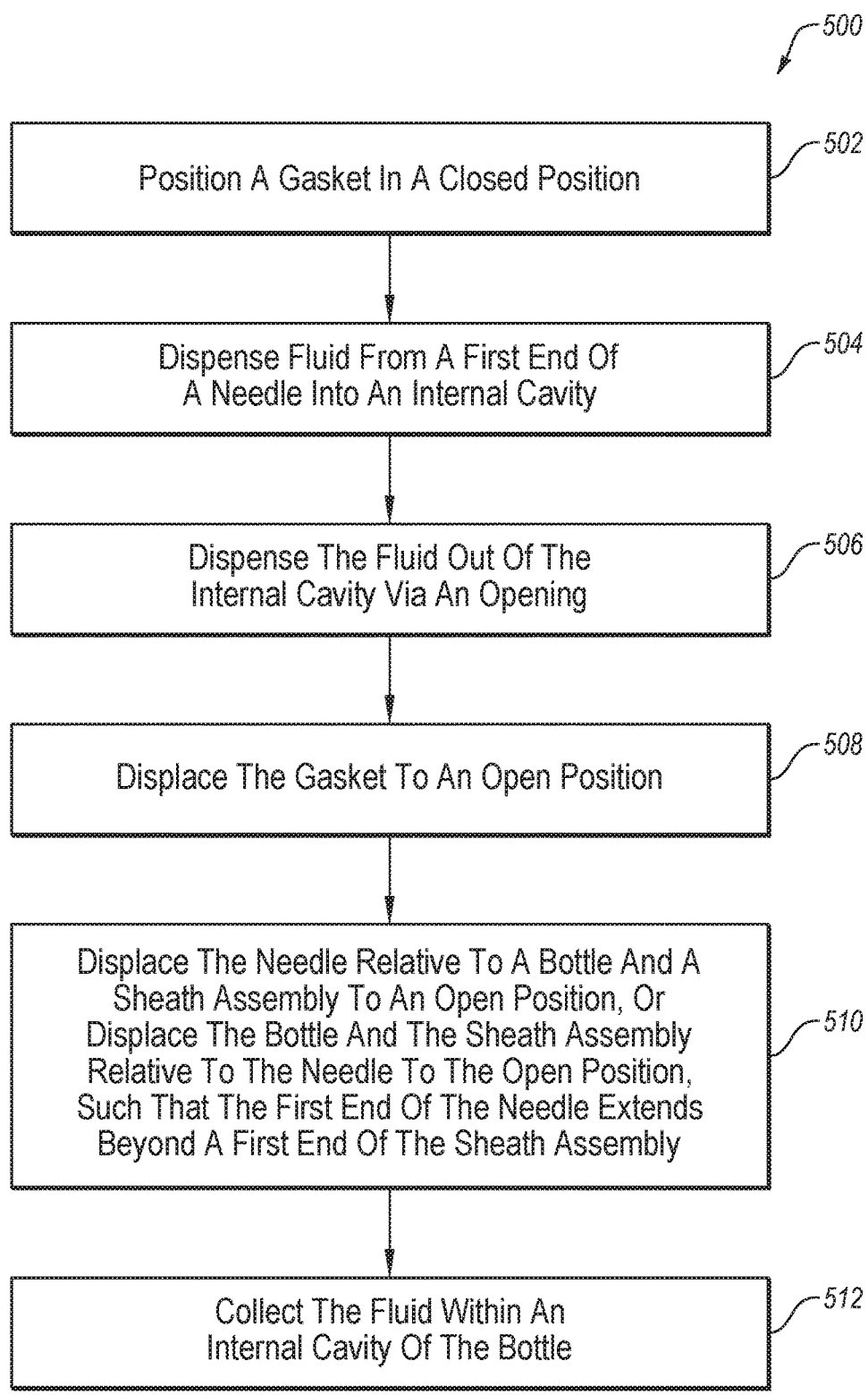
FIG. 5 illustrates a flow diagram of an example method to aseptically collect a fluid sample using a sampling system.

FIG. 5 illustrates a flow diagram of an example method 500 to aseptically collect a fluid sample using a sampling system, arranged in accordance with at least one embodiment described herein. The sampling system may include one or more of the sampling systems described herein, such as the systems 100, 200, 300, and 400 discussed elsewhere herein. In some embodiments, such sampling systems may include at least a needle, a sheath assembly, a gasket movable between an open position and a closed position, a bottle, and a movement system such as those described elsewhere herein.

The method 500 may be performed, in whole or in part, by the sampling systems 100, 200, 300, and 400 and/or by other sampling systems. Alternatively or additionally, the method 500 may be implemented by a processor device that performs or controls performance of one or more of the operations of the method 500. For instance, a computer (such as a computing device 600 of FIG. 6) or other processor device may be communicatively coupled to the sampling system and/or may be included as a control/sense system of the sampling system and may execute software or other computer-readable instructions accessible to the computer, e.g., stored on a non-transitory computer-readable medium accessible to the computer, to perform or control the sampling system to perform the method 500 of FIG. 5.

The method 500 may include one or more of blocks 502, 504, 506, 508, 510, 512, 514, and/or 516. Although illustrated as discrete blocks, various blocks may be divided into additional blocks, supplemented with additional blocks, combined into fewer blocks, or eliminated, depending on the particular implementation. The method 500 may begin at block 502.

In block 502 ("Position A Gasket In A Closed Position"), the gasket may be positioned in the closed position by the movement system. In some embodiments, the gasket may be positioned in the closed position to fluidly seal a first end of the sheath assembly. Block 502 may be followed by block 504.

In block 504 ("Dispense Fluid From A First End Of A Needle Into An Internal Cavity"), fluid may be dispensed from a first end of the needle into an internal cavity. In some embodiments, the internal cavity may be defined by the needle and the sheath assembly. Block 504 may be followed by block 506.

In block 506 ("Dispense The Fluid Out Of The Internal Cavity Via An Opening"), the fluid may be dispensed out of the internal cavity via an opening. In some embodiments, the opening may be defined by the sheath assembly. In these and other embodiments, the opening may be located above the first end of the needle relative to the direction of gravity. Block 506 may be followed by block 508.

In block 508 ("Displace The Gasket To An Open Position") the gasket may be displaced to the open position. In some embodiments, the gasket may be displaced to the open position to permit fluid to exit the internal cavity via the first end of the sheath assembly. Block 508 may be followed by block 510.

In block 510 ("Displace The Needle Relative To A Bottle And A Sheath Assembly To An Open Position, Or Displace The Bottle And The Sheath Assembly Relative To The Needle To The Open Position, Such That The First End Of The Needle Extends Beyond A First End Of The Sheath Assembly"), the needle may be displaced relative to the bottle and the sheath assembly to the open position, or the bottle and the sheath assembly may be displaced relative to the needle to the open position so that the first end of the needle extends beyond the first end of the sheath assembly and penetrates the septum and the needle is disposed within the internal cavity of the bottle. In some embodiments, the sheath assembly may remain at a fixed position and the needle may be displaced to extend beyond the first end of the sheath assembly. In these and other embodiments, the bottle may remain at a fixed position and displacement of the needle may result in the needle penetrating the septum of the bottle such that the first end of the needle is disposed within the internal cavity of the bottle. Block 510 may be followed by block 512.

In block 512 ("Collect The Fluid Within An Internal Cavity Of The Bottle"), the fluid may be collected within the internal cavity of the bottle.

One skilled in the art will appreciate that, for this and other processes, operations, and methods disclosed herein, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

In these and other embodiments, the method 500 may further include positioning the bottle so that the first end of the needle is positioned external to the bottle; positioning the sheath assembly so that the first end of the needle is disposed within the sheath assembly; and positioning the gasket in the closed position to fluidly seal the first end of the sheath assembly.

Alternatively or additionally, the method 500 may further include dispensing fluid from the first end of the needle into the internal cavity defined by the needle and the sheath assembly; and dispensing the fluid out of the internal cavity via the opening defined by the sheath assembly.

Figure 6:
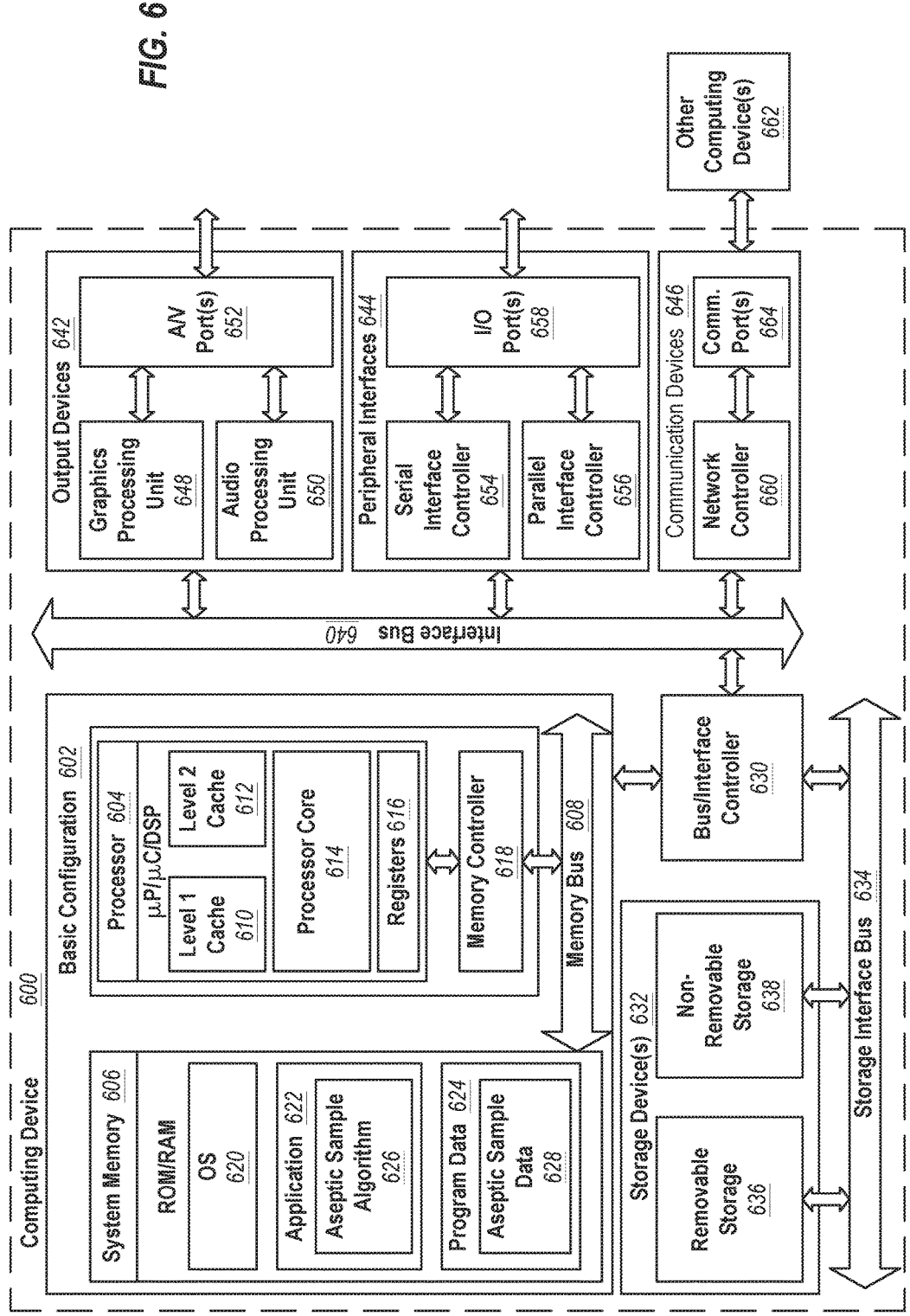
FIG. 6 illustrates a block diagram of an example computing device.

FIG. 6 illustrates a block diagram of an example computing device 600, arranged in accordance with at least one embodiment described herein. The computing device 600 may be used in some embodiments to perform or control performance of one or more of the methods and/or operations described herein. For instance, the computing device 600 may be communicatively coupled to and/or included in the systems 100, 200, 300, and 400 described herein to perform or control performance of the method 500 of FIG. 5. In a basic configuration 602, the computing device 600 typically includes one or more processors 604 and a system memory 606. A memory bus 608 may be used for communicating between the processor 604 and the system memory 606.

Depending on the desired configuration, the processor 604 may be of any type including, such as a microprocessor (µP), a microcontroller (µC), a digital signal processor (DSP), or any combination thereof. The processor 604 may include one or more levels of caching, such as a level one cache 610 and a level two cache 612, a processor core 614, and registers 616. The processor core 614 may include an arithmetic logic unit (ALU), a floating point unit (FPU), a digital signal processing core (DSP Core), or any combination thereof. An example memory controller 618 may also be used with the processor 604, or in some implementations the memory controller 618 may be an internal part of the processor 604.

Depending on the desired configuration, the system memory 606 may be of any type, such as volatile memory (such as RAM), non-volatile memory (such as ROM, flash memory, or the like), or any combination thereof. The system memory 606 may include an operating system 620, one or more applications 622, and program data 624. The application 622 may include an aseptic sample algorithm 626 that is arranged to schedule and/or conduct aseptic sampling operations associated with one or more of the sampling systems described herein. The program data 624 may include aseptic sample data 628 such as a schedule of sampling events, threshold values, and/or other data that may be used to control aspects of the sampling methods and/or operations described herein. In some embodiments, the application 622 may be arranged to operate with the program data 624 on the operating system 620 to perform one or more of the methods and/or operations described herein, including those described with respect to FIG. 5.

The computing device 600 may include additional features or functionality, and additional interfaces to facilitate communications between the basic configuration 602 and any other devices and interfaces. For example, a bus/interface controller 630 may be used to facilitate communications between the basic configuration 602 and one or more data storage devices 632 via a storage interface bus 634. The data storage devices 632 may include removable storage devices 636, non-removable storage devices 638, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer-readable instructions, data structures, program modules, or other data.

The system memory 606, the removable storage devices 636, and the non-removable storage devices 638 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 600. Any such computer storage media may be part of the computing device 600.

The computing device 600 may also include an interface bus 640 for facilitating communication from various interface devices (e.g., output devices 642, peripheral interfaces 644, and communication devices 646) to the basic configuration 602 via the bus/interface controller 630. The output devices 642 include a graphics processing unit 648 and an audio processing unit 650, which may be configured to communicate to various external devices such as a display or speakers via one or more A/V ports 652. The peripheral interfaces 644 include a serial interface controller 654 or a parallel interface controller 656, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 658. The communication devices 646 include a network controller 660, which may be arranged to facilitate communications with one or more other computing devices 662 over a network communication link via one or more communication ports 664.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 600 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 600 may also be implemented as a personal computer including both laptop computer and non-laptop computer configurations.

FIG. 7 is a block diagram illustrating an example operating environment 700 of a sampling system 705, arranged in accordance with at least one embodiment described herein. The operating environment 700 may include a system under test (SUT) 701, the sampling system 705, and a pump 703. The sampling system 705 may be the same as or similar to the systems 100, 200, 300, and 400 discussed above in relation to FIGS. 1-4C. The pump 703 may be fluidly coupled to the sampling system 705 and the SUT 701. Additionally, in some embodiments, the sampling system 705 may be fluidly coupled to the SUT 701 for return of fluid pumped when not being sampled.

The SUT 701 may produce and/or incorporate a fluid in its processes and provide the fluid to an external collector (not illustrated). The sampling system 705 may be configured to monitor the fluid to determine whether the fluid includes bacteria and/or contaminants at or below levels that are compliant with health and/or safety standards. Additionally or alternatively, one or more sensors may monitor the fluid. If a portion of the fluid appears to be above the levels of desired control and/or compliant with the health and/or safety standards, the sampling system 705 may collect a sample of the fluid for additional testing.

FIG. 8 is a block diagram of another example operating environment 800 of a sampling system 803, arranged in accordance with at least one embodiment described herein. The operating environment 800 may include a SUT 801, the sampling system 803, and a pump 805. The sampling system 803 may be the same as or similar to the sampling systems 100, 200, 300, 400, and 703 discussed above in relation to FIGS. 1-4C and 7. Additionally, the SUT 801 may be and may operate the same as or similar to the SUT 701 discussed above in relation to FIG. 7.

The pump 805 may be fluidly coupled to the SUT 801. The pump 805 may be fluidly coupled in line with the SUT 801 and the external collector (not illustrated). For example, the pump 805 may apply a pressure to the fluid to cause the fluid to traverse the SUT 801 and reach the external collector. Additionally, the sampling system 803 may not be fluidly coupled in line with the SUT 801 and the external collector. Furthermore, the SUT 801 may include a seal to fluidly seal the SUT 801 from the sampling system 803. In some embodiments, the sampling system 803 may be fluidly coupled to the pump 805 for return of fluid pumped when not sampled.

In some embodiments, if the fluid produced by the SUT 801 appears to be above the levels compliant with the health and/or safety standards, the SUT 801 may remove the seal and may become fluidly coupled to the sampling system 803. In these and other embodiments, pump 805 may apply the pressure to the fluid and cause the fluid to reach the sampling system 803. The sampling system 803 may collect the sample of the fluid and the SUT 801 may return the seal so as to fluidly seal the SUT 801 from the sampling system 803.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sampling system, comprising:
   a needle;
   a sample source configured to provide fluid to the needle;
   a sheath assembly that defines an opening, wherein the needle is disposed within the sheath assembly and the needle and the sheath assembly define an internal cavity between the needle and the sheath assembly;
   a gasket movable between an open position and a closed position relative to a first end of the sheath assembly, wherein the gasket is configured to be placed in the closed position to fluidly seal the first end of the sheath assembly to permit the fluid to exit a first end of the needle into the internal cavity and exit the internal cavity via the opening;
   a bottle positioned proximate to the first end of the sheath assembly, wherein the bottle includes a septum configured to fluidly seal an internal cavity of the bottle;

a movement system coupled to one or more of the bottle, the sheath assembly, the gasket, and the needle, the movement system configured to:
    displace the gasket to the open position to permit fluid to exit the internal cavity via the first end of the sheath assembly; and
    displace the needle relative to the bottle and the sheath assembly to an open position, or displace the bottle and the sheath assembly relative to the needle to an open position, such that the first end of the needle extends beyond the first end of the sheath assembly and penetrates the septum and the needle is disposed within the internal cavity of the bottle to permit the fluid to exit the first end of the needle into the internal cavity of the bottle.

2. The sampling system of claim 1, wherein at least one surface of the needle and the sheath assembly that define the internal cavity is coated with an antifouling material comprising at least one of silver; copper; gold; zinc; titanium; an alloy of any of the foregoing; organosilanes; quaternary ammonium compounds; fluorocarbons; parylene; and photocatalytic materials.

3. The sampling system of claim 1, further comprising one or more heat sources coupled to at least one of the needle and the sheath assembly, the heat sources configured to heat at least one of the needle and the sheath assembly.

4. The sampling system of claim 1, wherein the gasket comprises a polymer gasket that is infused with an antifouling material comprising at least one of silver; copper; gold; zinc; titanium; an alloy of any of the foregoing; organosilanes; quaternary ammonium compounds; fluorocarbons; parylene; and photocatalytic materials.

5. The sampling system of claim 1, wherein a surface normal of the septum is oriented at an angle not parallel to the direction of gravity.

6. The sampling system of claim 5, wherein the angle at which the surface normal of the septum is oriented is in a range between thirty and sixty degrees relative to the direction of gravity.

7. The sampling system of claim 5, wherein the opening is located above the first end of the needle relative to the direction of gravity.

8. The sampling system of claim 1, further comprising a light source positioned to emit light into the internal cavity, the light configured to inhibit development of bacteria within the internal cavity.

9. The sampling system of claim 8, wherein the light source is a light pipe and the light is ultraviolet (UV) light.

10. The sampling system of claim 1, the sampling system further comprising an O-ring configured to fluidly seal a second end of the sheath assembly.

11. The sampling system of claim 1, wherein the movement system is further configured to perform the following after the bottle collects a portion of the fluid from the needle:
    displace the needle relative to the bottle and the sheath assembly, or displace the bottle and the sheath assembly relative to the needle, such that the first end of the needle is positioned external to the bottle;
    displace the needle relative to the sheath assembly, or displace the sheath assembly relative to the needle, such that the first end of the needle is disposed within the sheath assembly; and
    displace the gasket to the closed position to fluidly seal the first end of the sheath assembly.

12. The sampling system of claim 11, wherein the movement system comprises a contactor plate configured to displace the gasket to the open position to permit fluid to exit the internal cavity via the first end of the sheath assembly.

13. The sampling system of claim 12, wherein the movement system is further configured to displace the bottle to contact the contactor plate to permit the contactor plate to displace the gasket to the open position.

14. The sampling system of claim 12, wherein the movement system further comprises a return plate and a spring, wherein the return plate and the spring are configured to position the gasket in the closed position to fluidly seal the first end of the sheath assembly.

15. The sampling system of claim 1, wherein the sampling system is fluidly coupled to a system under test, the system under test being fluidly coupled between a pump and the sampling system.

16. The sampling system of claim 1, wherein the sampling system is fluidly coupled to a pump, the pump being fluidly coupled between the sampling system and a system under test.

17. A method to collect a sample fluid using a sampling system that includes a needle, a sheath assembly, a gasket movable between an open position and a closed position, a bottle, and a movement system, the method comprising:
    positioning the gasket in the closed position to fluidly seal a first end of the sheath assembly;
    dispensing fluid from a first end of the needle into an internal cavity defined by the needle and the sheath assembly; and
    dispensing the fluid out of the internal cavity via an opening defined by the sheath assembly, wherein the opening is located above the first end of the needle relative to a direction of gravity.

18. The method of claim 17, further comprising:
    displacing the gasket to the open position to permit fluid to exit the internal cavity via the first end of the sheath assembly;
    displacing the needle relative to the bottle and the sheath assembly to the open position, or displacing the bottle and the sheath assembly relative to the needle to the open position, such that the first end of the needle extends beyond the first end of the sheath assembly and penetrates the septum and the needle is disposed within the internal cavity of the bottle; and
    collecting the fluid within the internal cavity of the bottle.

19. The method of claim 18, the method further comprising:
    displacing the needle relative to the bottle and the sheath assembly, or displacing the bottle and the sheath assembly relative to the needle, such that the first end of the needle is positioned external to the bottle;
    displacing the needle relative to the sheath assembly, or displacing the sheath assembly relative to the needle such that the first end of the needle is disposed within the sheath assembly; and
    displacing the gasket to the closed position to fluidly seal the first end of the sheath assembly.

20. The method of claim 18, the method further comprising:
    dispensing fluid from the first end of the needle into the internal cavity defined by the needle and the sheath assembly; and
    dispensing the fluid out of the internal cavity via the opening defined by the sheath assembly.

* * * * *